US012446956B2

(12) United States Patent
Cao et al.

(10) Patent No.: US 12,446,956 B2
(45) Date of Patent: Oct. 21, 2025

(54) RADIO FREQUENCY ABLATION DEVICE COMPRISING BALLOON BLOCKING CATHETER AND ABLATION METHOD THEREFOR

(71) Applicant: SHANGHAI GOLDEN LEAF MED TEC CO., LTD., Shanghai (CN)

(72) Inventors: Hongguang Cao, Shanghai (CN); Haidong Chen, Shanghai (CN); Meijun Shen, Shanghai (CN); Jiulin Guo, Shanghai (CN)

(73) Assignee: SHANGHAI GOLDEN LEAF MED TEC CO., LTD., Shanghai (CN)

( * ) Notice: Subject to any disclaimer, the term of this patent is extended or adjusted under 35 U.S.C. 154(b) by 580 days.

(21) Appl. No.: 17/929,592

(22) Filed: Sep. 2, 2022

(65) Prior Publication Data

US 2023/0181245 A1 Jun. 15, 2023

Related U.S. Application Data

(63) Continuation-in-part of application No. 16/064,934, filed as application No. PCT/CN2016/102980 on Oct. 22, 2016, now abandoned.

(30) Foreign Application Priority Data

Oct. 22, 2015 (CN) ........................ 201510689867.7
Oct. 22, 2015 (CN) ........................ 201520821938.X

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00577* (2013.01)

(58) Field of Classification Search
CPC ........ A61B 18/1492; A61B 2018/0022; A61B 2018/00577
See application file for complete search history.

(56) References Cited

U.S. PATENT DOCUMENTS

2011/0306878 A1* 12/2011 Desimone ................ A61N 1/30 600/431
2012/0071870 A1* 3/2012 Salahieh ............ A61B 1/00181 606/33
2017/0050041 A1* 2/2017 Cosman ................... A61N 1/36

* cited by examiner

*Primary Examiner* — Linda C Dvorak
*Assistant Examiner* — Abigail Bock
(74) *Attorney, Agent, or Firm* — George Guosheng Wang; Upstream Research and Patent LLC

(57) ABSTRACT

A radio frequency ablation device (300) comprising a balloon blocking catheter. The radio frequency ablation device (300) comprises a double or multi-lumen balloon blocking catheter (310) and a radio frequency ablation catheter (320). a stent (321) is arranged at the far end of the radio frequency ablation catheter (320). Two or more electrodes (322, 325, 326) are arranged on the stent (321), and are connected to a radio frequency generator respectively by means of the corresponding guide wires arranged in the radio frequency ablation catheter (320). When the radio frequency ablation device (300) is used for ablating blood vessel peripheral nerves, inflating a blocking balloon (311) arranged at the far end of the guide catheter (310) to block local blood flow in a blood vessel. The invention has ideal nerve ablation effect.

8 Claims, 10 Drawing Sheets

RADIO FREQUENCY ABLATION DEVICE COMPRISING BALLOON BLOCKING CATHETER AND ABLATION METHOD THEREFOR

BACKGROUND

Technical Field

The present invention relates to a radio frequency ablation device, and in particular, to a radio frequency ablation device comprising a balloon blocking guide catheter, and a radio frequency ablation method implemented by using the radio frequency ablation device, and belongs to the field of nerve ablation technologies.

Related Art

Abnormalities of a vegetative nerve play a very important role in occurrence, evolution, and development of many diseases. Recently, with the development of minimally invasive techniques, the nerve ablation technique gradually has been applied to the clinic to give treatments for symptoms such as hypertension, diabetes, heart diseases, and cancerous tumors, and has achieved good effects.

A radio frequency ablation catheter is an important device for conducting radio frequency ablation. A guide catheter is a tube disposed outside the radio frequency ablation catheter. The radio frequency ablation catheter usually needs assistance of the guide catheter to establish a path from the in vitro to the heart or the renal artery. During the ablation operation, most parts of the ablation catheter is kept inside the guide catheter.

In the existing technology, the radio frequency ablation device includes a radio frequency ablation instrument provided with a radio frequency generator, a radio frequency ablation catheter, and a radio frequency electrode that connected to an output terminal of the radio frequency generator by using a wire disposed inside the radio frequency ablation catheter, and further includes a return electrode connected to a loop terminal of the radio frequency generator. In the existing nerve ablation operation for a peripheral nerve of a renal artery, the return electrode of the radio frequency ablation device is usually disposed as a peripheral patch electrode, and is disposed in vitro. For a specific structure of the radio frequency ablation device, refer to the Chinese patent (Patent application number: CN200880126859.X) entitled "SYSTEM AND METHOD FOR MEASUREMENT OF IMPEDANCE USING CATHETER SUCH AS ABLATION CATHETER". As shown in FIG. 1, it discloses a catheter and a patch electrode system. A positive electrode of a radio frequency ablation generator 16 is electrically coupled to a point electrode 28T by using a source lead 46, a positive electrode of a sensing connector 32 is electrically coupled to the point electrode 28T by using a sensing lead 48, and a source loop $\mathbf{56}_1$ and a sensing loop $\mathbf{56}_2$ are respectively electrically connected to a negative electrode of the radio frequency ablation generator 16 and a negative electrode of the sensing connector. The source loop $\mathbf{56}_1$ and the sensing loop $\mathbf{56}_2$ are disposed in vitro. An excitation signal emitted by the point electrode 28T disposed inside the blood vessel needs to pass through the entire human tissue in vitro, and arrives at the radio frequency ablation generator 16 through the source loop $\mathbf{56}_1$. To be specific, a radio frequency current needs to enters the human tissue through walls of the blood vessels, and returns to the radio frequency ablation generator from the in vitro after passing through the entire human body loop. In short, the radio frequency current needs to pass through the entire human tissue. During the radio frequency ablation, a radio frequency direction of the radio frequency electrode is shown in FIG. 2. In the nerve ablation manner in which a radio frequency loop includes the human body, large human body impedance needs to be overcome. Therefore, large voltage, current, and radio frequency power need to be used, which inevitably injures the blood vessels of the human body.

In addition, in the existing technology, there is a device in which a radio frequency electrode and a return electrode are disposed on a same support to ablate pathological tissues, for example, a scissor radio frequency ablation device provided in the Chinese patent (Patent application number: CN201210128849.8) entitled "MULTIFUNCTIONAL RADIO FREQUENCY COOLING KNIFE". As shown in FIG. 8, the multifunctional radio frequency cooling knife includes a first branch 10, a second branch 20, a connection end portion 30, and an operation handle 40. Two bipolar radio frequency electrodes are disposed on each of the first branch 10 and the second branch 20. A radio frequency signal between two bipolar radio frequency electrodes disposed on each branch enters inside the tissue from the outside of the tissue through the human tissue, and returns to a local radio frequency loop outside the tissue for radio frequency ablation. In the radio frequency ablation device, the radio frequency electrode and the return electrode are both disposed inside the human body but outside the target portion. During the ablation process, no flowing blood affecting the radio frequency loop exists near the target portion. When the ablation catheter in which the radio frequency electrode and the return electrode are both disposed on a same support is directly placed inside the renal artery to ablate a nerve plexus near the vessel, because flowing blood exists inside the renal artery, conductivity of the blood affects formation of the radio frequency loop. As a result, it is not easy to form a loop between two electrodes and passing through the blood vessel wall or the tissue outside the vessel, and in this case, it is difficult to achieve the ideal effect during ablation of the nerve near the renal artery.

SUMMARY

The primary technical problem to be resolved in the present invention is to provide a radio frequency ablation device comprising a balloon blocking guide catheter.

Another technical problem to be resolved by the present invention is to provide a radio frequency ablation method implemented by using the radio frequency ablation device.

To achieve the foregoing invention objective, the following technical solutions are used in the present invention.

A radio frequency ablation device, comprising a balloon blocking guide catheter of a dual-lumen or multi-lumen catheter, a radio frequency ablation catheter and a control handle, wherein, the balloon blocking guide catheter has an inflatable blocking balloon disposed at a far end thereof, the radio frequency ablation catheter has a stent disposed on a far end of the balloon blocking guide catheter, a plurality of radio frequency electrodes and at least one return electrode on the stent to perform radio frequency ablation, and a through-wall electrode that is hollow and configured to inject liquid or gas into a blood vessel wall, during a radio frequency ablation process, the blocking balloon is inflated to block local blood flow inside the blood vessel, liquid or gas is infused into the blood vessel at the target portion through the through-wall electrode, and an electrical loop is formed between the radio frequency electrode and the return electrode.

Preferably, the through-wall electrode comprises a delivery part, a transform part and a bent part in serial, the delivery part connects with a control handle, for withdrawing or pushing forwardly the through-wall electrode, and the bent part provides a sharp end to penetrate the blood vessel wall for sending the liquid or gas into the blood vessel wall.

Preferably, the radio frequency ablation catheter further has a connecting tube has a plurality of openings to provides fluids into the blood vessel.

Preferably, the bent part biases from the transform part and the delivery part so as to be suitable for entering the blood vessel wall.

Preferably, the through-wall electrode is disposed at an adherent location in the middle of a segment-shaped stent, or the through-wall electrode is disposed at a front segment of a strip-shaped puncture needle.

Preferably, the through-wall electrode also serves as a radio frequency electrode or a return electrode.

A radio frequency ablation method, used to ablate a peripheral nerve of a blood vessel by using the radio frequency ablation device aforesaid, wherein the blocking balloon is inflated to block local blood flow inside the blood vessel, liquid or gas is infused into the blood vessel at the target portion through the through-wall electrode, and an electrical loop is formed between the radio frequency electrode and the return electrode to perform radio frequency ablation Preferably, the liquid delivered from the through-wall electrode and that from the connecting tube are configured to provide synergistic efficacy.

Preferably, liquid/gas used to change resistance of the blood vessel wall is injected into the blood vessel wall before radio frequency ablation.

Preferably, the liquid/gas is used to reduce temperature of the blood vessel wall.

The radio frequency ablation device provided in the present invention includes a balloon blocking guide catheter. The blocking balloon disposed on the far end of the guide catheter is inflated for blocking, so that local blood flow during radio frequency ablation can be blocked. Liquid/gas is infused into the blood vessel, so that the temperature environment and/or conductivity environment inside the blood vessel can be changed. In the radio frequency ablation device, no peripheral electrode needs to be used, and the loop passing through the blood vessel wall can be formed between the radio frequency electrode and the return electrode disposed on the stent, to conduct radio frequency ablation. Because the blood vessel wall is close to the nerve, and no conductivity is implemented in the lumen, a radio frequency loss is small, and an optimal radio frequency ablation effect is achieved. In addition, liquid/gas used to reduce local resistance may be further injected into the blood vessel wall through the hollow through-wall electrode, to increase a conductivity degree and a conductivity probability when the electrodes pass through the blood vessel wall, and reduce a degree and probability of conductivity between the electrodes inside the blood vessel during radio frequency ablation. In addition, liquid is infused into the blood vessel and the blood vessel wall, so that a local temperature can be reduced, and a local blood vessel can be protected.

DETAILED DESCRIPTION

The following gives a detailed description with reference to the accompanying drawings and specific embodiments. For the convenience of description, an end close to a manipulator (away from a target portion) is referred to as a near end, and an end away from the manipulator (close to the target portion) is referred to as a far end.

To change an ablation mode in the existing technology that when a peripheral nerve of a lumen is ablated, a peripheral patch electrode needs to be disposed in vitro as a return electrode, and the peripheral patch electrode and the radio frequency electrode form a human body loop to conduct radio frequency ablation. The present invention provides a radio frequency ablation device 300 shown in FIG. 4 and FIG. 5 and comprising a balloon blocking guide catheter, a radio frequency ablation catheter, and a radio frequency generator (not shown in the figure), and further provides a radio frequency ablation method for ablating a peripheral nerve of a lumen by using the radio frequency ablation device. The radio frequency ablation device and the radio frequency ablation method may be used to give a radio frequency treatment to a cavity tissue, for example, ablation treatment to a vein, an endometrium, and an esophagus.

Figure 1:
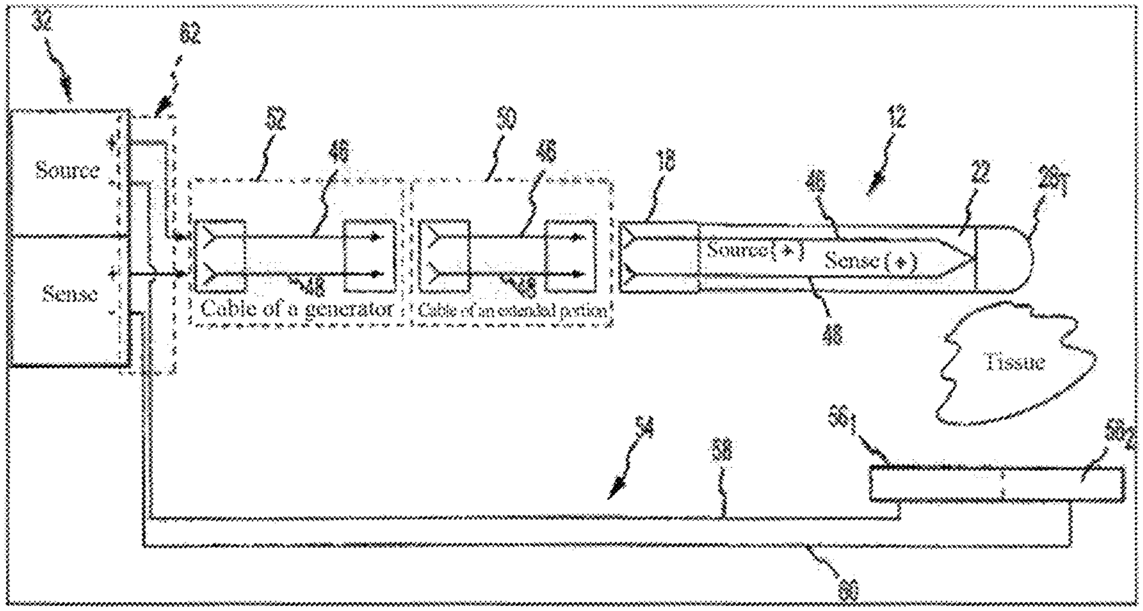
FIG. 1 is a schematic structural diagram of a radio frequency ablation system using a peripheral patch electrode as a return electrode in the existing technology.
Figure 2:
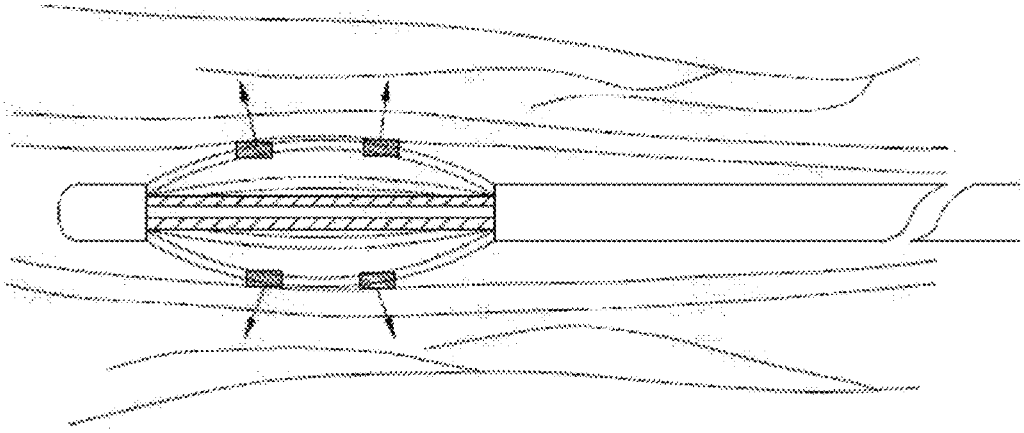
FIG. 2 is shows a radio frequency direction when a radio frequency is released to a lumen in the radio frequency ablation system shown in FIG. 1.
Figure 3:
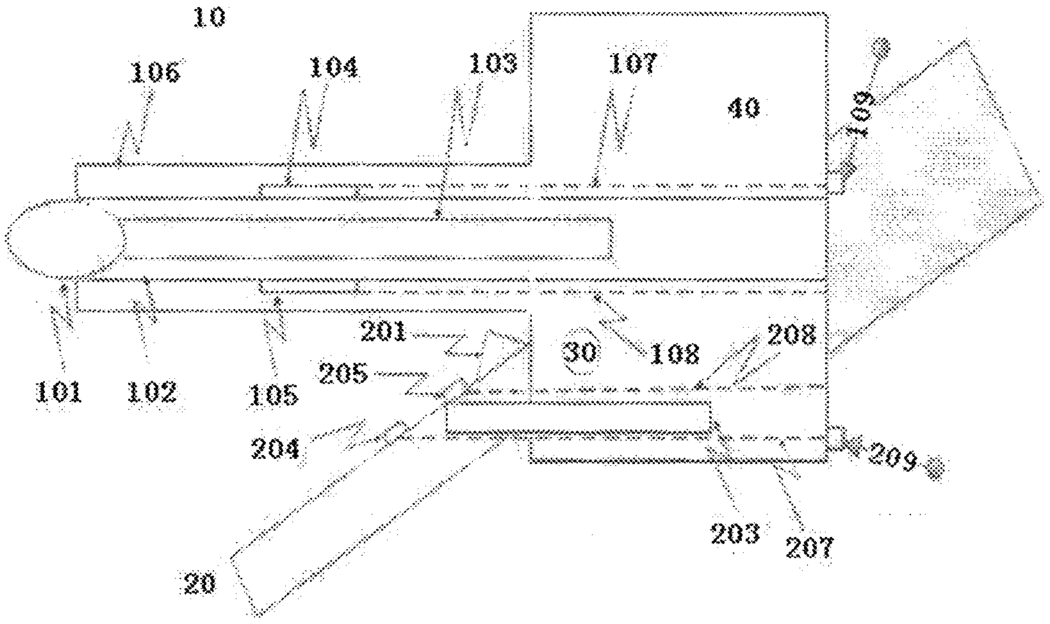
FIG. 3 is a schematic structural diagram of a radio frequency cooling knife used to cut off or ablate a pathological tissue from the outside of the pathological tissue in another existing technology.
Figure 4:
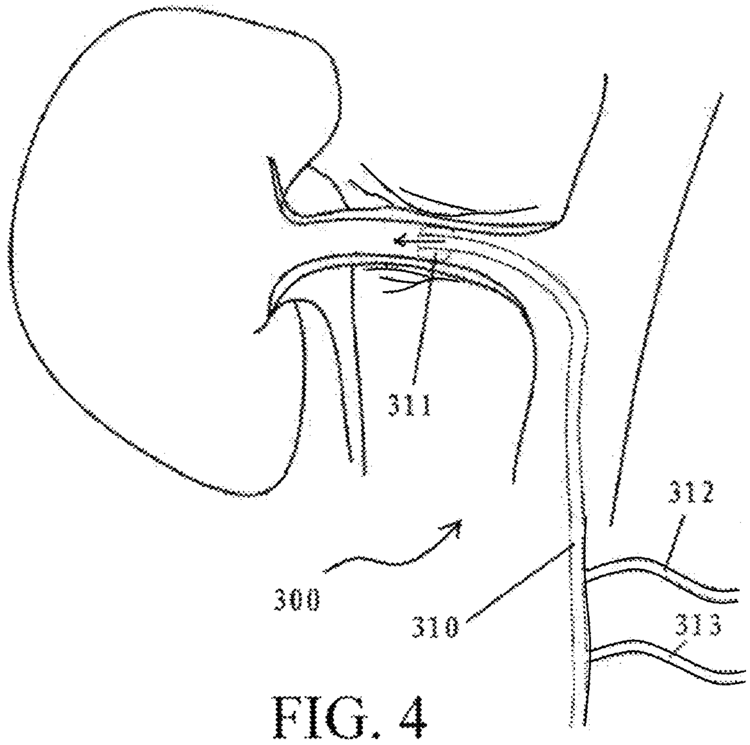
FIG. 4 is a schematic diagram of a basic structure of a balloon blocking guide catheter according to the present invention.

As shown in FIG. 4, the balloon blocking guide catheter 310 is a dual-lumen or multi-lumen catheter. An inflatable blocking balloon 311 is disposed on an outer wall of a far end (namely, an end entering inside the human body) of a guide catheter 310. A first catheter branch 312 communicating with a first lumen inside the guide catheter is disposed on a near end (namely, an end away from the human body) of the guide catheter, the inside of the blocking balloon 311 communicates with the first lumen inside the guide catheter 310, and the first catheter branch 312 is used to provide a inflation material for the blocking balloon 311 through the first lumen. Specifically, an inflation device (not shown in the figure) connected to a tail end of the first catheter branch 312 infuses gas or liquid into the blocking balloon 311, to implement an inflation effect of the blocking balloon 311. A second catheter branch 313 communicating with a second lumen (namely, an infusion lumen) inside the guide catheter 310 is further disposed on the near end of the guide catheter 310. An infusion port is disposed on a far end of the infusion lumen, and the infusion lumen is used to infuse liquid/gas into a blood vessel on a target portion through the infusion port. An infusion device (not shown in the figure) is connected to a tail end of the second catheter branch 313, and is used to infuse liquid, for example, a contrast agent, into the blood vessel on the target portion through the second catheter branch 313, the infusion lumen, and the infusion port. For an infusion direction, refer to an arrow inside the blood vessel in FIG. 4. In addition, gas, for example, $CO_2$, may be alternatively infused into the blood vessel on the target portion. The blocking balloon 311 may be aligned with the infusion port on the far end of the guide catheter 1, or a distance may exist between the blocking balloon 311 and the infusion port on the far end of the guide catheter 1, to help blocking flowing blood inside the blood vessel and infuse liquid/gas into the blood vessel. In the balloon blocking guide catheter 310, local blood flow inside the blood vessel on the target portion can be blocked by inflating the blocking balloon 311 on the far end, and a temperature environment or a conducting environment inside the blood vessel on the target portion can be changed by infusing liquid (for example, non-conductive liquid) into the blood vessel on the target portion.

Figure 5:
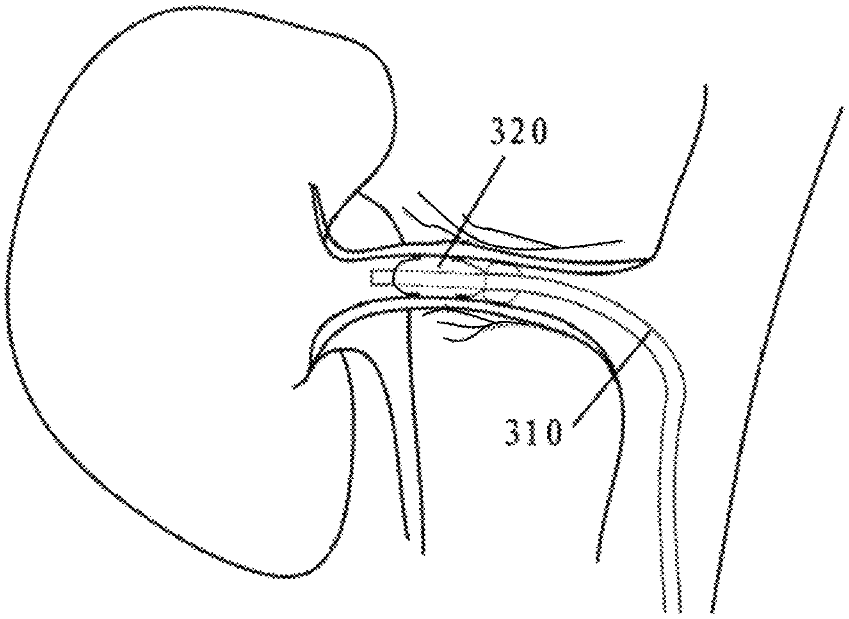
FIG. 5 is a schematic diagram of a working state when a radio frequency ablation catheter passes through the balloon blocking guide catheter shown in FIG. 4.

As shown in FIG. 5, the radio frequency ablation catheter 320 is disposed in a particular lumen, for example, the second lumen, inside the balloon blocking guide catheter 310, so that liquid/gas can be infused into the blood vessel on the target portion through a gap between the radio frequency ablation catheter 320 and the second lumen. Alternatively, the radio frequency ablation catheter 320 may be disposed in another lumen other than the first lumen and the second lumen inside the balloon blocking guide catheter 310. a stent 321 is disposed on a far end of the radio frequency ablation catheter 320, and at least two electrodes 322 are disposed on the stent 321. The stent 321 can expand and contract. When the stent 321 expands, some or all of the multiple electrodes 322 abut against the wall. The electrodes 322 may be connected, through a corresponding lead inside the radio frequency ablation catheter, to the radio frequency generator disposed inside a radio frequency ablation instrument. At least one of the multiple electrodes 322 is a radio frequency electrode 325, and the radio frequency electrode 325 is connected to an output terminal of the radio frequency generator. At least one electrode is a return electrode 326, and the return electrode 326 is connected to a loop terminal of the radio frequency generator. Multiple radio frequency electrodes 325 may share one return electrode 326 to form an electrical loop. When the conductivity environment inside the blood vessel changes, the radio frequency ablation instrument controls different electrodes 322 on the far end of the radio frequency ablation catheter 320 to be conducted, so that the electric loop passing through a blood vessel wall can be formed between a corresponding radio frequency electrode and return electrode, to conduct radio frequency. Therefore, in the radio frequency ablation device, no peripheral patch electrode needs to be used to form the electrical loop with the human body.

Figure 10A:
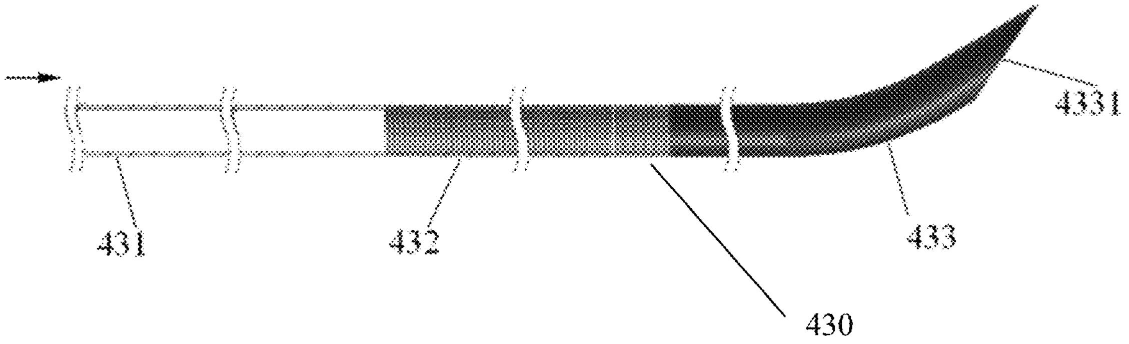
FIG. 10A is an enlarged schematic diagram of the through-wall electrode.
Figure 14:
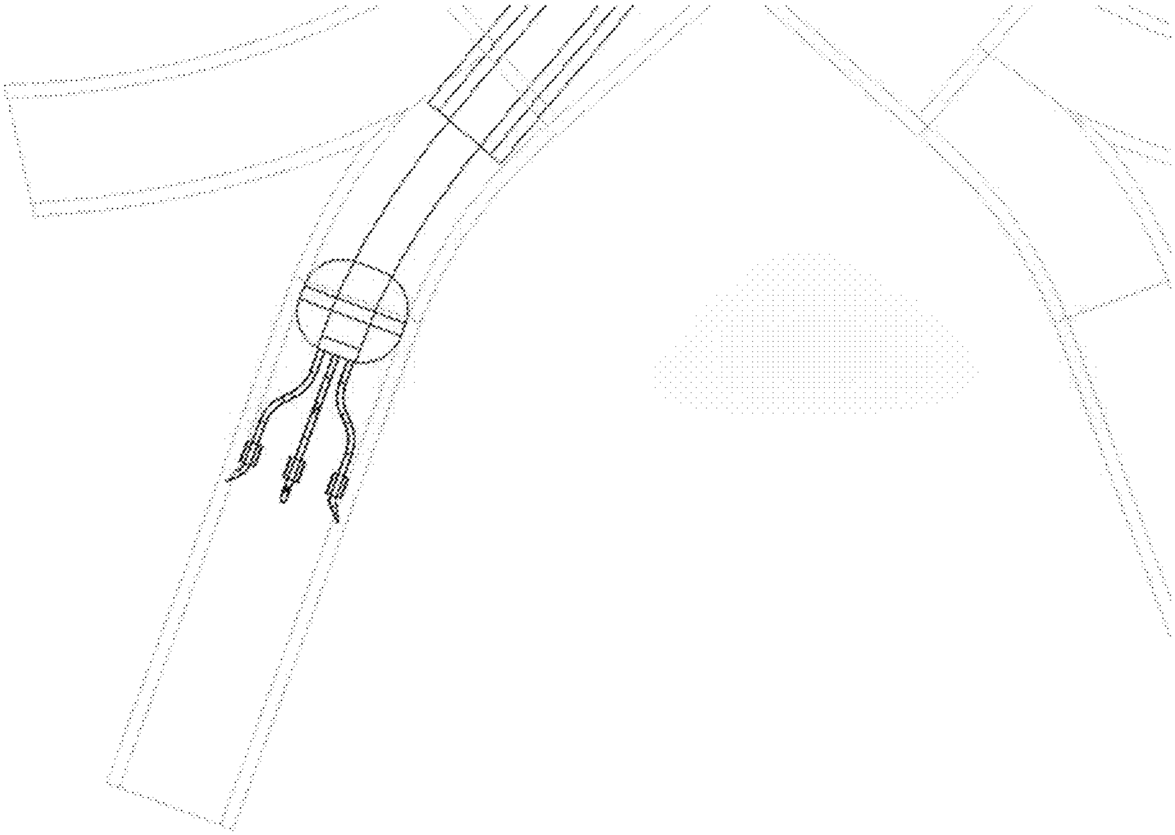

As is shown in FIG. 10A and FIG. 14, one or more through-wall electrodes may further be disposed on the far end of the radio frequency ablation catheter 320. The through-wall electrode may be disposed on the stent, or the through-wall electrode may be directly disposed on a strip-shaped connection catheter of the radio frequency ablation catheter. The through-wall electrode is hollow and communicates with a path inside the radio frequency ablation catheter, and is used to inject liquid/gas into the blood vessel wall. For example, when the stent is segment-shaped, the through-wall electrode may be disposed at an adherent location in the middle of the segment-shaped stent. For another example, when a shape of the stent is a strip-shaped puncture needle, the through-wall electrode may be directly disposed at a front segment of the strip-shaped puncture needle. When the through-wall electrode is disposed on the stent, the through-wall electrode may be independently disposed, and the through-wall electrode may also serve as a radio frequency electrode or a return electrode.

The following describes the radio frequency ablation device provided in the present invention and a radio frequency ablation principle thereof with reference to FIG. 6 to FIG. 14.

Embodiment 1

Figure 6:
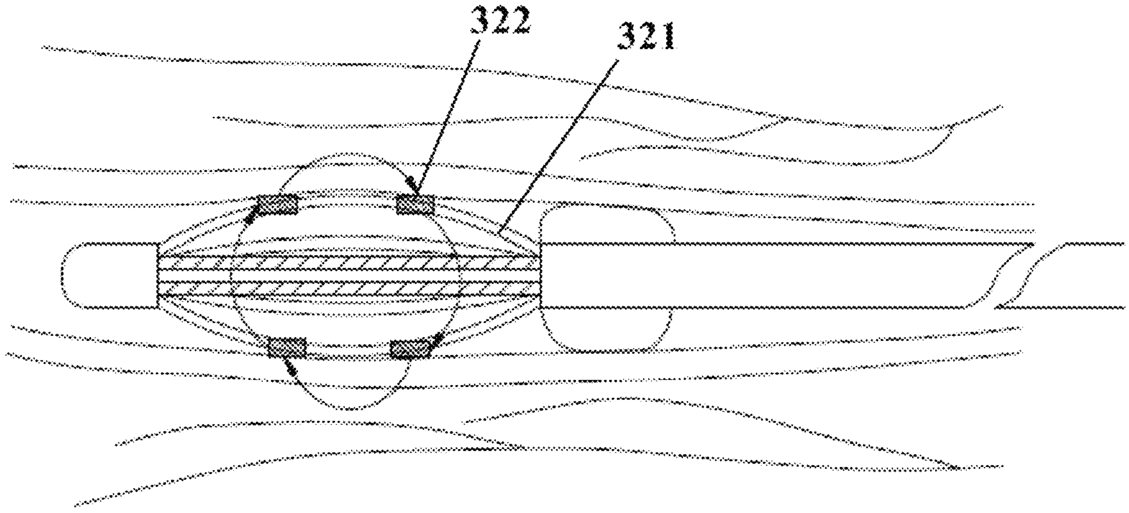
FIG. 6 is a principle diagram of radio frequency ablation after the radio frequency ablation device provided in the present invention is used and a non-conductive liquid is infused into a lumen of a target portion.

As shown in FIG. 6, the radio frequency ablation device includes a guide catheter 310 and a radio frequency ablation catheter 320, and further includes a radio frequency ablation instrument (not shown in the figure) used to control a radio frequency process. The radio frequency ablation catheter 320 is connected to the radio frequency ablation instrument. The radio frequency ablation catheter 320 includes a strip-shaped connection catheter, a stent 321 disposed on a far end of the connection catheter, and a control handle 10 disposed on a near end of the connection catheter. During use, the control handle 10 is connected to the radio frequency ablation instrument through a composite cable, and multiple leads used to connect different electrodes and a radio frequency generator are disposed in the composite cable. Multiple electrodes 322 are disposed on the stent 321. After a front end of the radio frequency ablation catheter 320 extends out of the guide catheter 310, and the multiple electrodes are adherent under the action of the control handle 10, the radio frequency instrument may separately control different electrodes 322 on the front end of the radio frequency ablation catheter 320, to release a radio frequency. After a conductivity environment inside the blood vessel on the target portion is changed, during the radio frequency releasing process, a loop can be formed by using a blood vessel wall between different electrodes to conduct radio frequency ablation. In the radio frequency ablation device, no peripheral patch electrode needs to be used.

Figure 7:
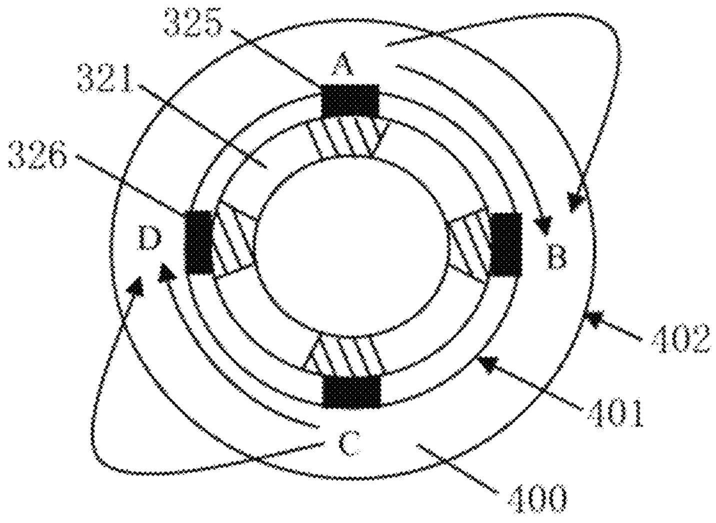
FIG. 7 is a schematic diagram of the radio frequency ablation principle shown in FIG. 6 on a cross section of a blood vessel.

As shown in FIG. 6 and FIG. 7, after the inflated blocking balloon 311 blocks the local blood flow in the blood vessel on the target portion, a contrast agent or other non-conductive liquid is infused into the lumen on the target portion through the second catheter branch 313, to control the radio frequency electrode to be adherent, and the radio frequency electrode 325 and the return electrode 326 may form a loop through the blood vessel wall, to conduct radio frequency. In this case, as shown in FIG. 7, some radio frequency currents may enter into a blood vessel wall 400 through the radio frequency electrode 325 inside the lumen, and returns back to the return electrode 326 inside the lumen after passing through the blood vessel wall 400 between an inner surface 401 and an outer surface 402 of the blood vessel wall. At the same time, some radio frequency currents may pass through the blood vessel wall 400 from the inner surface 401 of the blood vessel wall, pass through the outer surface 402 of the blood vessel wall, enters the blood vessel wall 400 from the outside of the outer surface 402 of the blood vessel wall, and then, returns to the return electrode 326 through the blood vessel wall 400. During this process, a ratio of the some radio frequency currents flowing between the inner surface 401 and the outer surface 402 of the blood vessel wall to the some radio frequency currents passing through the blood vessel wall and entering the blood vessel wall depends on a difference between conductivity of the blood vessel wall and conductivity of a peripheral tissue of the blood vessel wall.

In this case, because the contrast agent is a poor conductor, and has high resistance, an environment inside the lumen is a non-conductive environment, and is in a non-conducted state. In this case, a peripheral electrode needs to be used, and mutual electron motion can be implemented between electrodes through the blood vessel wall, to implement radio frequency. A radio frequency emission direction between electrodes can be controlled by controlling a radio frequency sequence of the electrodes, to implement radio frequency ablation on nerve tissues on different ports of the outside of the blood vessel wall. When the foregoing solution is used, the blood vessel wall is a conductor, and because the blood vessel wall is close to the nerve, there is a small radio frequency loss, and the ideal radio frequency ablation effect of the nerve is achieved. Therefore, it is appropriate to infuse liquid used to reduce conductivity, for example, non-conductive liquid, into the blood vessel in which blood flow is blocked, and good nerve ablation effect can be achieved. In addition, the non-conductive liquid infused into the lumen of the blood vessel can further reduce the temperature of the local lumen, and protect the local blood vessel. Certainly, gas may be alternatively infused into the blood vessel in which blood flow is blocked, to achieve a same objective.

Figure 8:
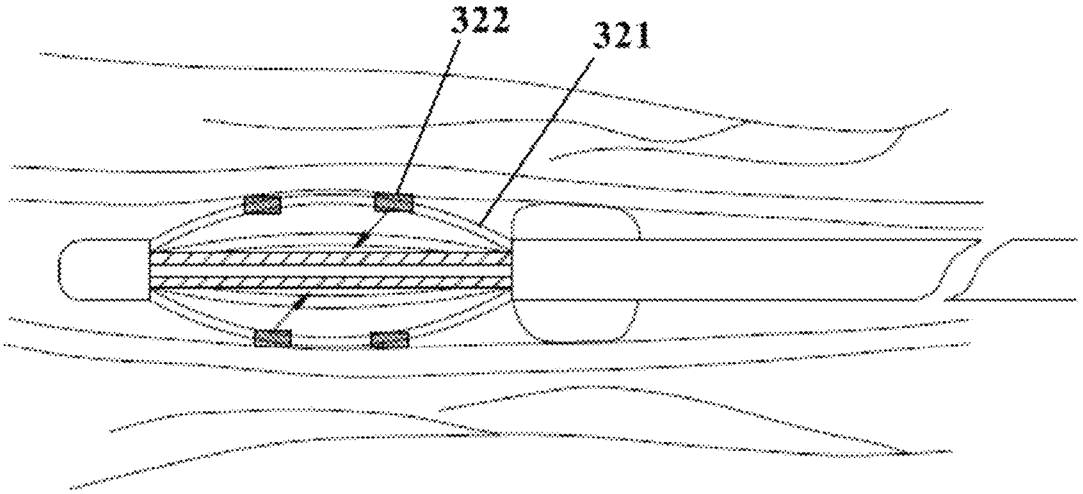
FIG. 8 is a principle diagram of radio frequency ablation after the radio frequency ablation device provided in the present invention is used and a conductive liquid is infused into a lumen of a target portion.

As shown in FIG. 8, liquid or gas may be infused into the blocking balloon 311 through the first catheter branch 312, to implement an inflation effect of the blocking balloon 311, and block blood flow in the blood vessel. Normal saline may be infused into the blood vessel on the target portion through the second catheter branch 313. After the normal saline or other conductive liquid is infused into the blood vessel on the target portion through the second catheter branch 313, when the radio frequency electrode is adherent and emits a radio frequency current, because the normal saline is conductive, an environment in the lumen is a conductive environment, and communication is implemented in the lumen, electrons of the electrode freely moves inside the blood vessel, to form a loop inside the lumen. In some nerve ablation operations, normal saline needs to be infused into the blood vessel. In this case, liquid/gas used to reduce local resistance of the blood vessel wall may be injected into the blood vessel wall, so that the blood vessel wall has good conductivity relative to the environment inside the blood vessel. Therefore, an ablation loop similar to that shown in FIG. 6 and FIG. 7 can be formed in the blood vessel wall and the peripheral tissue thereof, thereby achieving the nerve tissue ablation effect.

Embodiment 2

Figure 10B:
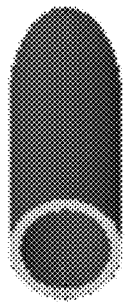
FIG. 10B is a side-view from an angle indicated by the arrow showing in FIG. 10A.
Figure 11:
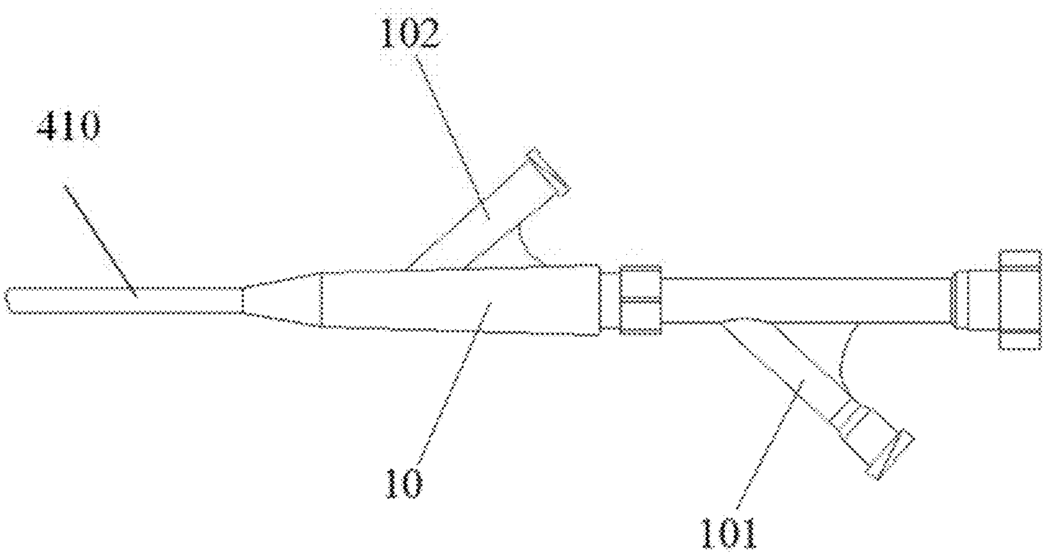
FIG. 11 is a schematic diagram of a control handle of the present invention.

In this embodiment, a structure of the radio frequency ablation device is basically the same as that in Embodiment 1, and includes the balloon blocking guide catheter, a radio frequency ablation catheter, and a radio frequency ablation instrument connected to the radio frequency ablation catheter. A difference between Embodiment 2 and Embodiment 1 lies in that a hollow through-wall electrode is further disposed on a far end of the radio frequency ablation catheter. As is shown in FIG. 10A and FIG. 10B, the through-wall electrode is hollow and communicates with an internal path of the radio frequency ablation catheter, and is used to inject liquid used to change resistance of a blood vessel wall into the blood vessel wall. For example, normal saline used to reduce the resistance may be infused. The through-wall electrode may be a radio frequency electrode or a return electrode disposed on a stent, or may be a separately disposed electrode dedicated for injection.

An outlet is disposed on a far end of the through-wall electrode, an inlet is disposed on a near end of the through-wall electrode, and the inlet communicates with the internal path of the radio frequency ablation catheter. An infusion tube communicating with the internal path is disposed on a rear end of the radio frequency ablation catheter, and the infusion tube is connected to an infusion device. The infusion device may inject, through the hollow through-wall electrode and the infusion tube, a material used to reduce local resistance of a blood vessel wall, for example, normal saline, into a wall tissue near a radio frequency ablation point, to increase a conductivity degree and a conductivity probability when the electrodes pass through the blood vessel wall, and reduce a degree and probability of conductivity between the electrodes inside the blood vessel during radio frequency ablation.

Therefore, during the radio frequency ablation process, the blocking balloon disposed on the far end of the guide catheter is inflated to block local blood flow inside the blood vessel, liquid/gas used to reduce conductivity inside the blood vessel is infused into the blood vessel through the guide catheter, and at the same time, liquid used to reduce local resistance is injected into the wall tissue of the blood vessel through the hollow through-wall electrode, and then, a loop may be formed between the radio frequency electrode and the return electrode through the blood vessel wall by controlling different electrodes of the radio frequency ablation catheter, to conduct radio frequency ablation. Therefore, the nerve ablation effect is better than that in Embodiment 1.

Specifically, the through-wall electrode disposed on the far end of the radio frequency ablation catheter 2 may be disposed at an adherent location in the middle of a segment-shaped radio frequency electrode, or may be disposed at a front segment of a strip-shaped puncture needle radio frequency electrode. In addition, a front end of the through-wall electrode is a sharp acute angle and may have an edge, a shape of the through-wall electrode is a cone, a rhombus, or the like, a length range of the through-wall electrode is preferably 0.01 to 20 mm, and a diameter range of the through-wall electrode is preferably 0.01 to 2.0 mm.

Embodiment 3

In this embodiment, to inject liquid used to reduce local resistance into a blood vessel wall on a target portion, a hollow puncture needle is disposed on a front end of the radio frequency ablation catheter, to replace an injection function of the hollow through-wall electrode in Embodiment 2. A through-wall electrode or a common electrode disposed in this embodiment only has a radio frequency ablation function, or may have a hollow structure and have an injection function. After the through-wall electrode penetrates or passes through the blood vessel wall, the through-wall electrode may directly release energy to a nerve plexus near the blood vessel wall, to reduce injury caused to the blood vessel wall during the radio frequency process. For introduction of the through-wall electrode, refer to the description made by the applicant in the prior patent application "CATHETER AND DEVICE FOR NERVE ABLATION IN CAVITY-PASSING AND WALL-PENETRATING MODE AND METHOD FOR NERVE ABLATION" (patent application number: CN201310049148.X). In this embodiment, the remaining structure of the radio frequency ablation device is basically the same as that in Embodiment 2, and includes the balloon blocking guide catheter, the radio frequency ablation catheter, and a radio frequency ablation instrument connected to the radio frequency ablation catheter.

A liquid cavity communicating with the puncture needle is disposed in the radio frequency ablation catheter provided in this embodiment, and is connected to an external infusion device through a catheter branch. The infusion device may inject, through the catheter branch and puncture needle, a material used to reduce local resistance of a blood vessel wall, for example, normal saline, into a wall tissue near a radio frequency ablation point, to increase a conductivity degree and a conductivity probability when the electrodes pass through the blood vessel wall, and reduce a degree and probability of conductivity between the electrodes inside the blood vessel during radio frequency ablation.

Therefore, during the radio frequency ablation process, the blocking balloon disposed on the far end of the guide catheter is inflated to block local blood flow inside the blood vessel, liquid/gas used to reduce conductivity inside the blood vessel is infused into the blood vessel through the guide catheter, and preferably, liquid/gas used to reduce conductivity is infused, to reduce a conductivity environment and a temperature environment inside the blood vessel on the target portion. At the same time, liquid used to reduce local resistance of the blood vessel wall is injected into a blood vessel wall tissue through the puncture needle. Then, a loop may be formed between the radio frequency electrode and the return electrode through the blood vessel wall by controlling different electrodes of the radio frequency ablation catheter, to conduct radio frequency ablation. Therefore, the nerve ablation effect is better than that in Embodiment 1.

To sum up, in the radio frequency ablation device provided in the present invention and comprising the balloon blocking guide catheter, the blocking balloon on the far end of the balloon blocking guide catheter is inflated, so that local blood flow inside the blood vessel on the target portion can be blocked. Liquid/gas used to change the conductivity environment or temperature environment is infused into the blood vessel on the target portion, and different electrodes of the radio frequency ablation catheter are controlled, so that a loop can be formed between the radio frequency electrode and the return electrode through the blood vessel wall or the peripheral tissue thereof, to conduct radio frequency. In the radio frequency ablation device using the guide catheter, a radio frequency emission direction between electrodes can be controlled without a peripheral electrode, and the loop is formed between different electrodes through the blood vessel wall, to conduct radio frequency ablation. Compared with a loop passing through the entire human body, the loop formed between the radio frequency electrode and the return electrode and passing through the blood vessel wall is a loop formed in a partial area, and needs to overcome small impedance of the human body. Because the blood vessel wall is close to the nerve, and no conductivity is implemented inside the chamber, a radio frequency loss is small, and an ideal nerve ablation effect is achieved.

In addition, liquid/gas used to reduce local resistance may be further infused into the blood vessel wall through the hollow through-wall electrode or the puncture needle, to increase a conductivity degree and a conductivity probability when the electrodes pass through the blood vessel wall, and reduce a degree and probability of conductivity between the electrodes inside the blood vessel during radio frequency ablation. In addition, liquid is injected into the blood vessel and the blood vessel wall tissue, so that a local temperature can be reduced, and a local blood vessel can be protected.

The radio frequency ablation instrument in the present invention has a multi-channel radio frequency output function, and a loop can be formed between multiple electrodes and through the blood vessel wall. The radio frequency ablation instrument loads radio frequency energy to a blood vessel, muscle, and nerve attached to the ablation catheter through various electrodes of the ablation catheter, and a radio frequency current sequentially passes through the blood vessel wall and the return electrode, and returns to the radio frequency ablation instrument, to form a radio frequency loading loop. The radio frequency current generates high-speed ion vibration in the attached tissues, and generates a temperature rise, to achieve an ablation objective.

In the technical solution provided in the present invention, by using the foregoing radio frequency ablation instrument, a partial radio frequency current loop can be formed between two electrodes through the blood vessel wall, and the radio frequency energy is released only between two electrodes forming the loop, and a temperature is generated, thereby greatly reducing much radio frequency energy consumed by human body impedance.

A working principle of the radio frequency ablation instrument has been described in detail in the two prior patent applications: "RADIO FREQUENCY ABLATION METHOD AND RADIO FREQUENCY ABLATION SYSTEM FOR NERVE ABLATION" (patent application number: CN201410035836.5) and "RADIO FREQUENCY ELECTRODE WITH TEMPERATURE MEASUREMENT FUNCTION AND IMPEDANCE MEASUREMENT FUNCTION AND ABLATION INSTRUMENT" (patent application number: CN201310530007.X), and details are not described herein again.

Embodiment 4

Figure 9:
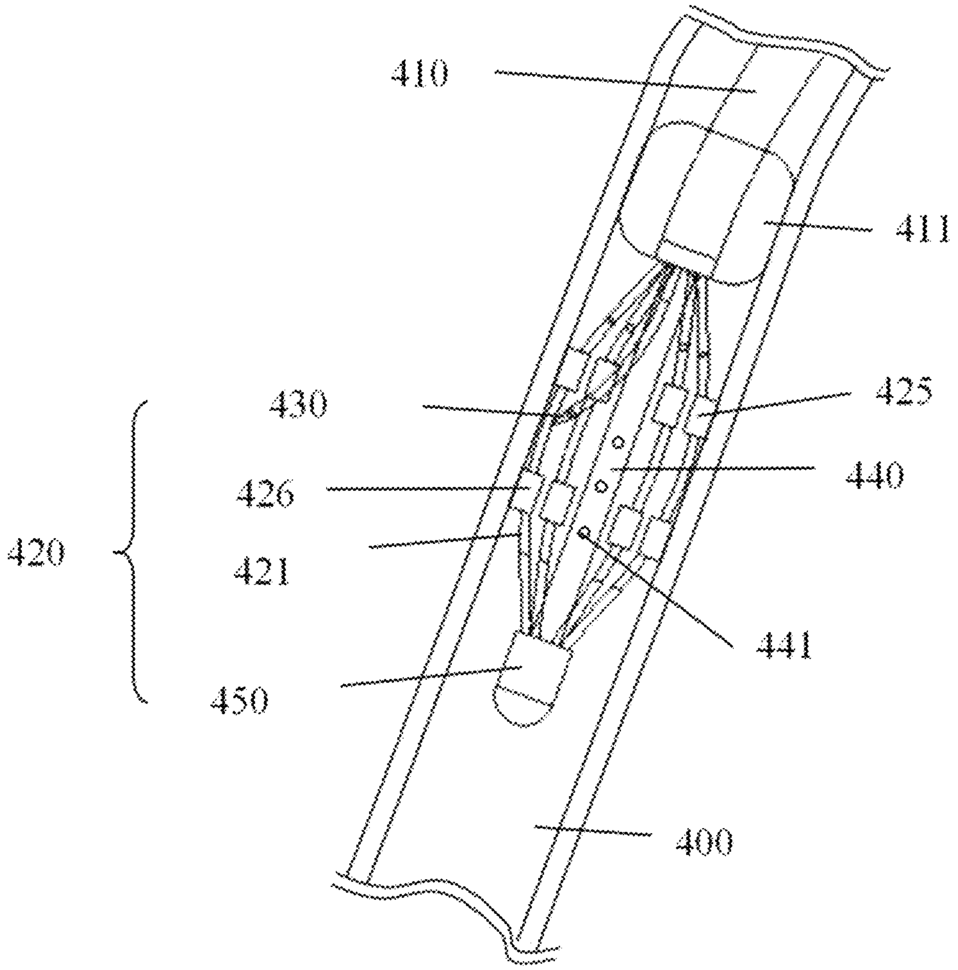
FIG. 9 is an alternative schematic diagram of a balloon blocking guide catheter according to the present invention.

As shown in FIG. 9, the radio frequency ablation device includes a balloon blocking guide catheter 410, a radio frequency ablation catheter 420 and a control handle 10.

During a radio frequency ablation process, the blocking balloon 411 is inflated to block local blood flow inside the blood vessel, liquid or gas is infused into the blood vessel at the target portion through the through-wall electrode 430, and an electrical loop is formed between the radio frequency electrode 425 and the return electrode 426.

The balloon blocking guide catheter 410 is of a dual-lumen or multi-lumen catheter, and has a blocking balloon 411 disposed at a far end thereof. The inflatable blocking balloon 411 used to block blood flow inside a blood vessel is disposed on an outer wall of a far end of the guide catheter. The balloon blocking guide catheter 410 is similar to the balloon blocking guide catheter 310 in the first embodiment.

The radio frequency ablation catheter 420 comprises a resilient stent 421, a cap 450, a connecting tube 440, a plurality of radio frequency electrodes 425, at least one return electrode 426, and a through-wall electrode 430. The resilient stent 421 is fixed at a far end of the balloon blocking guide catheter 410 and shifts between a withdrawing status and an expanding status. The radio frequency electrodes 425 and the return electrode 426 are fixed to the stent 421 for RF ablation. The cap 450 locates at a far end of the stent 421, capping the stent 421 and the connecting tube 440 together. The connecting tube 440 is movable along the balloon blocking guide catheter 410, to withdraw or stretch the stent 421. Alternatively, the connecting tube 440 has openings 441 to provides fluids into the blood vessel.

In case of the withdrawing status, the stent 421 is compact for delivering the balloon blocking guide catheter 410 within the blood vessel.

In case of the expanding status, the stent 421 expands outwardly, so that the radio frequency electrodes 425 and the return electrode 426 reliably adhere to the blood vessel wall 400. The through-wall electrode 430 extends along a particular lumen of the multi-lumen and outside the balloon blocking guide catheter 410 and extend outwardly from the stent 421 into the blood vessel wall 400.

As is shown in FIG. 10A and FIG. 10B, the hollow through-wall electrode 430 comprises a delivery part 431, a transform part 432 and a bent part 433 in serial. The delivery part 431 connects with a control handle 10 (referring to FIG. 11) so as to be controlled by an operator, for withdrawing or pushing forwardly the through-wall electrode 430. The delivery part 431 is braided from metals (nickel-titanium, platinum-tungsten or the like), or woven from polymers (PI, PEEK or the like). The transform part 432 is made of a metal spring tube. The bent part 433 is cut from a metal tube to provide a sharp end 4331 to penetrate the blood vessel wall 400. The through-wall electrode 430 is hollow to send liquid or gas into the blood vessel wall 400. The control handle 10 provides a first input 101 for controlling the connecting tube to move forwardly or backwardly, and a second input 102 connecting with the first catheter branch for delivering the liquid or gas.

In particularly, the transform part 432 connects the bent part 433 to the delivery part 431, and is stretchable to resiliently push the bent part 433 into the blood vessel wall 400. Moreover, the transform part 432 is adapted to tortuous blood vessels since it is made of a thin spring tube.

The bent part 433 biases from the transform part 432 and the delivery pat 431 so as to be suitable for entering the blood vessel wall. As is explicitly shown in FIG. 10B, the sharp end 4331 of the bent part 433 forms a sharp acute angle, therefore being able to go deeper into the blood vessel wall 400.

The liquid or gas can be delivered through the delivery part 431, the transform part 432 and the bent part 433, and be infused into the blood vessel wall 400 to reduce conductivity inside the blood vessel on the target portion. Preferably, the liquid or gas used to change resistance of the blood vessel wall is injected into the blood vessel wall before radio frequency ablation.

The liquid or gas injected into the blood vessel wall before radio frequency ablation is also used to change a temperature environment inside the blood vessel, or provide synergistic efficacy with the fluid input from the openings 441. Thus, the radio frequency ablation could be more effective and safer.

Figure 12:
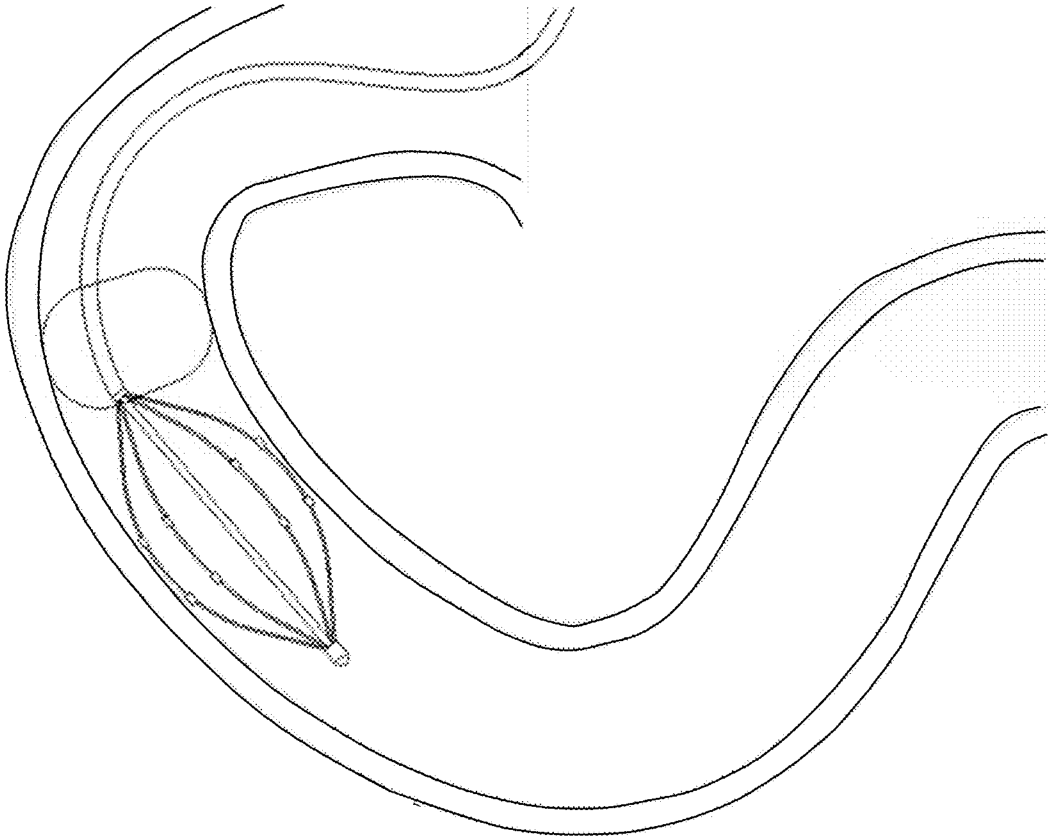
FIG. 12 is a schematic diagram of a radio frequency ablation catheter to achieve ablation in the duodenum.
Figure 13:
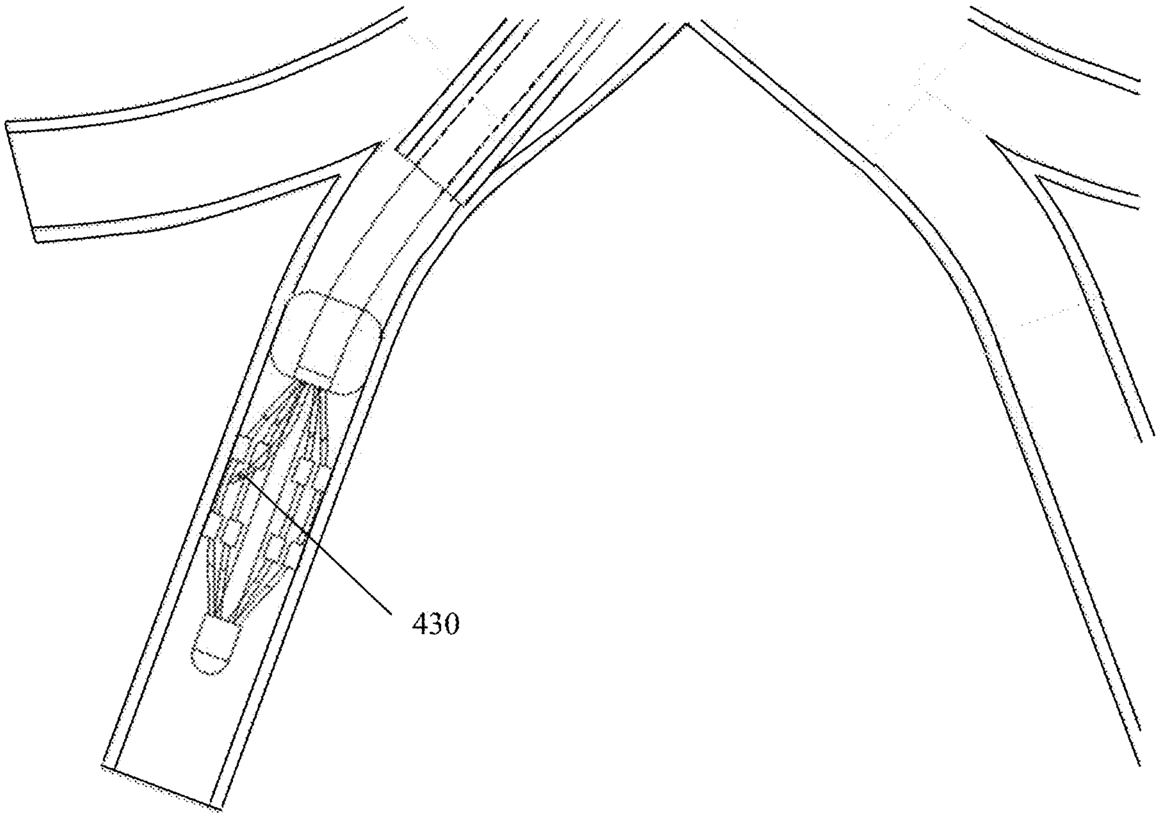
FIG. 13 is a schematic diagram of a radio frequency ablation catheter with a puncture needle to achieve ablation in the bronchus; and, FIG. 14 is a schematic diagram of a radio frequency ablation catheter with multiple puncture needles to achieve ablation in the bronchus.

Although it is illustrated by a RF ablation to a blood vessel of a renal artery, it is well known that the present invention could be applied to ablate other nerves, blood vessels, or lumen. In an intervention medical operation, the radio frequency ablation catheter 420 is delivered to the target location of the cavernous organ, such as the duodenum, the bronchus, etc. FIG. 12 is a schematic diagram of a radio frequency ablation catheter to achieve ablation in the duodenum. With the expansion of the stent 421, the through-wall electrode 430 goes into the intestinal wall of the duodenum, then the fluid or gas is perfused through the through-wall electrode 430 into the intestinal wall in order to peel off the submucosa. Finally, the radio frequency electrodes 425 and the return electrode 426 perform RF ablation in order to destroy the submucosa and achieve endothelial reconstruction. Similarly, FIG. 13 is a schematic diagram of a radio frequency ablation catheter with a puncture needle to achieve ablation in the bronchus.

In another embodiment shown in FIG. 14, the radio frequency ablation catheter 320 in the blood vessel/bronchus/duodenum has a plurality of through-wall electrodes/puncture needles. One or more through-wall electrodes are disposed at the front segment of the strip-shaped puncture needle. These through-wall electrodes/puncture needles form a petal-like shape, with a portion of the puncture needles with through-wall electrodes for penetrating into or through the wall of the tube and another portion of the puncture needles for injecting fluid into the tube.

Of course, it is also possible to achieve endothelial reconstruction merely by ablating only without perfusion; or merely by perfusing alcohol through the through-wall electrode 430 in order to destroy the mucosal layer.

It should be noted that the technical features of each of the above embodiments can be combined in any number of ways. In order to make the description concise, not all possible combinations of the technical features of each of the above embodiments have been described. However, as long as the combinations of these technical features are not contradictory, they should be considered to be within the scope of the present invention.

The foregoing has described in detail the radio frequency ablation device comprising a balloon blocking guide catheter, and the ablation method thereof in the present invention. Any obvious modification made by a person of ordinary skill in the art without departing from the essential of the present invention is invasion of patent right of the present invention, and shall undertake the legal liability.

What is claimed is:

1. A radio frequency ablation device, comprising a balloon blocking guide catheter of a dual-lumen or multi-lumen catheter, a radio frequency ablation catheter and a control handle, wherein, the balloon blocking guide catheter has an inflatable blocking balloon disposed at a far end thereof, the radio frequency ablation catheter has a stent disposed on a far end of the balloon blocking guide catheter, a plurality of radio frequency electrodes and at least one return electrode on the stent to perform radio frequency ablation, and a through-wall electrode that is hollow and configured to inject liquid or gas into a blood vessel wall, the blocking balloon is configured to be inflated to block local blood flow inside the blood vessel during a radio frequency ablation process, the through-wall electrode is configured to infuse liquid or gas into the blood vessel at the target portion so as to form an electrical loop between the radio frequency electrode and the return electrode through a blood vessel wall, wherein some radio frequency currents enter into the blood vessel wall through the radio frequency electrode and returns back to the return electrode after passing through the blood vessel wall between an inner surface and an outer surface of the blood vessel wall, some radio frequency currents pass through the blood vessel wall from the inner surface of the blood vessel wall, pass through the outer surface of the blood vessel wall, enters the blood vessel wall from the outside of the outer surface of the blood vessel wall, and then, returns to the return electrode through the blood vessel wall, the through-wall electrode comprises a delivery part, a transform part and a bent part in serial, the delivery part connects with a control handle, for withdrawing or pushing forwardly the through-wall electrode, the bent part provides a sharp end to penetrate the blood vessel wall for sending the liquid or gas into the blood vessel wall, the through-wall electrode is disposed at a front segment of a strip-shaped puncture needle, and the bent part that is configured to be cut from a metal tube to provide a sharp end to penetrate the blood vessel wall.

2. The radio frequency ablation device according to claim 1, wherein the radio frequency ablation catheter further has a connecting tube has a plurality of openings to provides fluids into the blood vessel.

3. The radio frequency ablation device according to claim 1, wherein the bent part biases from the transform part and the delivery part so as to be suitable for entering the blood vessel wall.

4. The radio frequency ablation device according to claim 3, wherein the through-wall electrode is configured to serves as a radio frequency electrode or a return electrode.

5. A radio frequency ablation method, used to ablate a peripheral nerve of a blood vessel by using the radio frequency ablation device according to claim 1, wherein the blocking balloon is inflated to block local blood flow inside the blood vessel, liquid or gas used to reduce resistance of the blood vessel wall is infused into the blood vessel at the target portion through the through-wall electrode into a blood vessel wall, and an electrical loop is formed between the radio frequency electrode and the return electrode to perform radio frequency ablation, wherein some radio frequency currents enter into the blood vessel wall through the radio frequency electrode and returns back to the return electrode after passing through the blood vessel wall between an inner surface and an outer surface of the blood vessel wall, some radio frequency currents pass through the blood vessel wall from the inner surface of the blood vessel wall, pass through the outer surface of the blood vessel wall, enters the blood vessel wall from the outside of the outer surface of the blood vessel wall, and then, returns to the return electrode through the blood vessel wall.

6. The radio frequency ablation method according to claim 5, wherein the liquid delivered from the through-wall electrode and that from the connecting tube are configured to provide synergistic efficacy.

7. The radio frequency ablation method according to claim 5, wherein liquid/gas used to reduce resistance of the blood vessel wall is injected into the blood vessel wall before radio frequency ablation.

8. The radio frequency ablation method according to claim 7, wherein the liquid/gas is used to reduce temperature of the blood vessel wall.

* * * * *